United States Patent [19]
Bock et al.

[11] 4,390,703
[45] Jun. 28, 1983

[54] INTERMEDIATES FOR THE RESOLUTION OF SOME INTERPHENYLENE-9-THIA-11-OXO-12-AZAPROSTANOIC ACIDS

[75] Inventors: Mark G. Bock, Hatfield; Robert M. Di Pardo, Lansdale, both of Pa.

[73] Assignee: Merck & Co., Inc., Rahway, N.J.

[21] Appl. No.: 276,117

[22] Filed: Jun. 22, 1981

[51] Int. Cl.³ .......................................... C07D 277/04
[52] U.S. Cl. ...................... 548/187; 548/186
[58] Field of Search ........................................ 548/187

[56] References Cited
U.S. PATENT DOCUMENTS
4,225,609  9/1980  Cragoe, Jr. et al. ............... 424/270

OTHER PUBLICATIONS

B. Halpern et al., Chem. Abstracts 65:19996(e), (1966).
Gerlach, Helv. Chem. Acta, 1987-1593, (1969), English Translation.

Primary Examiner—Nicholas S. Rizzo
Assistant Examiner—M. C. Eakin
Attorney, Agent, or Firm—Alice O. Robertson; Ernest V. Linek; Daniel T. Szura

[57] ABSTRACT

Some derivatives of interphenylene-9-thia-11-oxo-12-azaprostanoic acid which are active renal vasodilator agents are resolved via diastereomeric camphanyl or camphorcarbonyl esters. Upon hydrolysis, the separated diastereoisomers yield optically pure enantiomers.

3 Claims, No Drawings

INTERMEDIATES FOR THE RESOLUTION OF SOME INTERPHENYLENE-9-THIA-11-OXO-12-AZA-PROSTANOIC ACIDS

BACKGROUND OF THE INVENTION

Resolution is the process whereby a racemic modification, be it racemic mixture, racemic compound or racemic solution, is separated into its enantiomers. The most popular method consists in converting the enantiomers of a racemic modification into diastereoisomers which in turn are separated e.g., by fractional crystallization or chromatography. Thus, e.g. racemic acids may be separated by optically active bases, and racemic alcohols resolved by optically active acids or derivatives thereof.

Interphenylene-9-thia-11-oxo-12-azaprostanoic acids having pharmaceutical activity are described in U.S. Pat. No. 4,225,609. It has now been discovered that racemic mixtures of these acids can be resolved to provide individual enantiomers of the acids using camphanic acid or a camphorcarboxylic acid as the resolving agent. The resolution proceeds through formation of ester diastereomers, separation of the diastereomers and subsequent hydrolysis to obtain the corresponding enantiomeric acids.

SUMMARY OF THE INVENTION

The unique process of the present invention relates to the resolution of derivatives of interphenylene-9-thio-11-oxo-12-azaprostanoic acid, illustrated by the formula

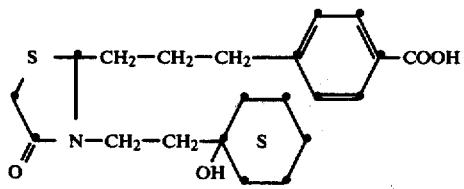

using camphanic acid or a camphorcarboxylic acid as the resolving agent.

DETAILED DESCRIPTION OF THE INVENTION

The present invention relates to a unique process for resolving a selected group of renal vasodilator agents, i.e., interphenylene-9-thia-11-oxo-12-azaprostanoic acids having the structural formula:

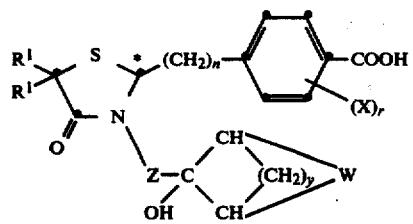

wherein
(a) the asterisk (*) marks the asymmetric carbon;
(b) X is chlorine or methyl;
(c) r is 0, 1 or 2;
(d) n is 3 or 4;
(e) R' is hydrogen, deuterium or methyl;
(f) Z is ethylene, trimethylene, cis or trans-propenylene or propynylene;
(g) Y is 0, 1 or 2; and
(h) W is polymethylene of 2–6 carbon atoms.

Examples of Formula I compounds are:
4-{3-[3-[2-(1-hydroxycyclohexyl)ethyl]-4-oxo-2-thiazolidinyl]propyl} benzoic acid;
4-{3-[3-[2-(1-hydroxycyclopentyl)ethyl]-4-oxo-2-thiazolidinyl]propyl} benzoic acid;
4-{3-[3-[2-(1-hydroxycycloheptyl)ethyl]-4-oxo-2-thiazolidinyl]propyl} benzoic acid;
4-{3-[3-[2-(1-hydroxy-4,4-dimethylcyclohexyl)-ethyl]-4-oxo-2-thiazolidinyl]propyl}-benzoic acid;
4-{3-[3-[2-(9-hydroxy-9-bicyclo[3.3.1]nonyl)ethyl]-4-oxo-2-thiazolidinyl]propyl}-benzoic acid;
4-{4-[3-[2-(1-hydroxycyclohexyl)ethyl]-4-oxo-2-thiazolidinyl]butyl} benzoic acid;
4-{3-[3-[3-(1-hydroxycyclohexyl)propyl]-4-oxo-2-thiazolidinyl]propyl} benzoic acid;
4-{3-[3-[3-(1-hydroxycyclohexyl)-trans-2-propenyl]-4-oxo-2-thiazolidinyl]propyl} benzoic acid;
4-{3-[3-[3-(1-hydroxycyclohexyl)-cis-2-propenyl]-4-oxo-2-thiazolidinyl]propyl} benzoic acid;
4-{3-[3-[3-(1-hydroxycyclohexyl)-2-propynyl]-4-oxo-2-thiazolidinyl]propyl} benzoic acid;
4-{3-[3-[2-(1-hydroxycyclohexyl)ethyl]-4-oxo-2-thiazolidinyl]propyl}-3-chlorobenzoic acid;
4-{3-[3-[2-(1-hydroxycyclohexyl)ethyl]-4-oxo-2-thiazolidinyl]propyl}-2-chlorobenzoic acid;
4-{3-[3-[2-(1-hydroxycyclohexyl)ethyl]-4-oxo-2-thiazolidinyl]propyl}-3-methylbenzoic acid;
4-{3-[3-[2-(1-hydroxycyclohexyl)ethyl]-5,5-dimethyl-4-oxo-2-thiazolidinyl]propyl} benzoic acid;
4-{3-[3-[2-(1-hydroxycyclohexyl)ethyl]-5,5-dideuterio-4-oxo-2-thiazolidinyl]propyl} benzoic acid
and the like.

The above-described compounds, their use and the method of preparation thereof are disclosed in U.S. Pat. No. 4,225,609.

The resolution process comprises
(a) protecting the benzoic acid function of the Formula I compound e.g., by treating the acid with an alcohol or an alkyl halide in the presence of a catalyst to form an ester;
(b) treating the product from step (a) with an optically active esterifying agent in the presence of a catalyst and a base to format least one separable diastereomeric ester;
(c) separating the diastereomeric esters into individual diastereoisomers; and
(d) recovering the Formula I enantiomer from the individual corresponding diastereoisomers e.g., by hydrolysis in the presence of a catalyst in a suitable solvent.

The following flow sheet, illustrates the resolution process:

FLOW SHEET OF EXAMPLE 1
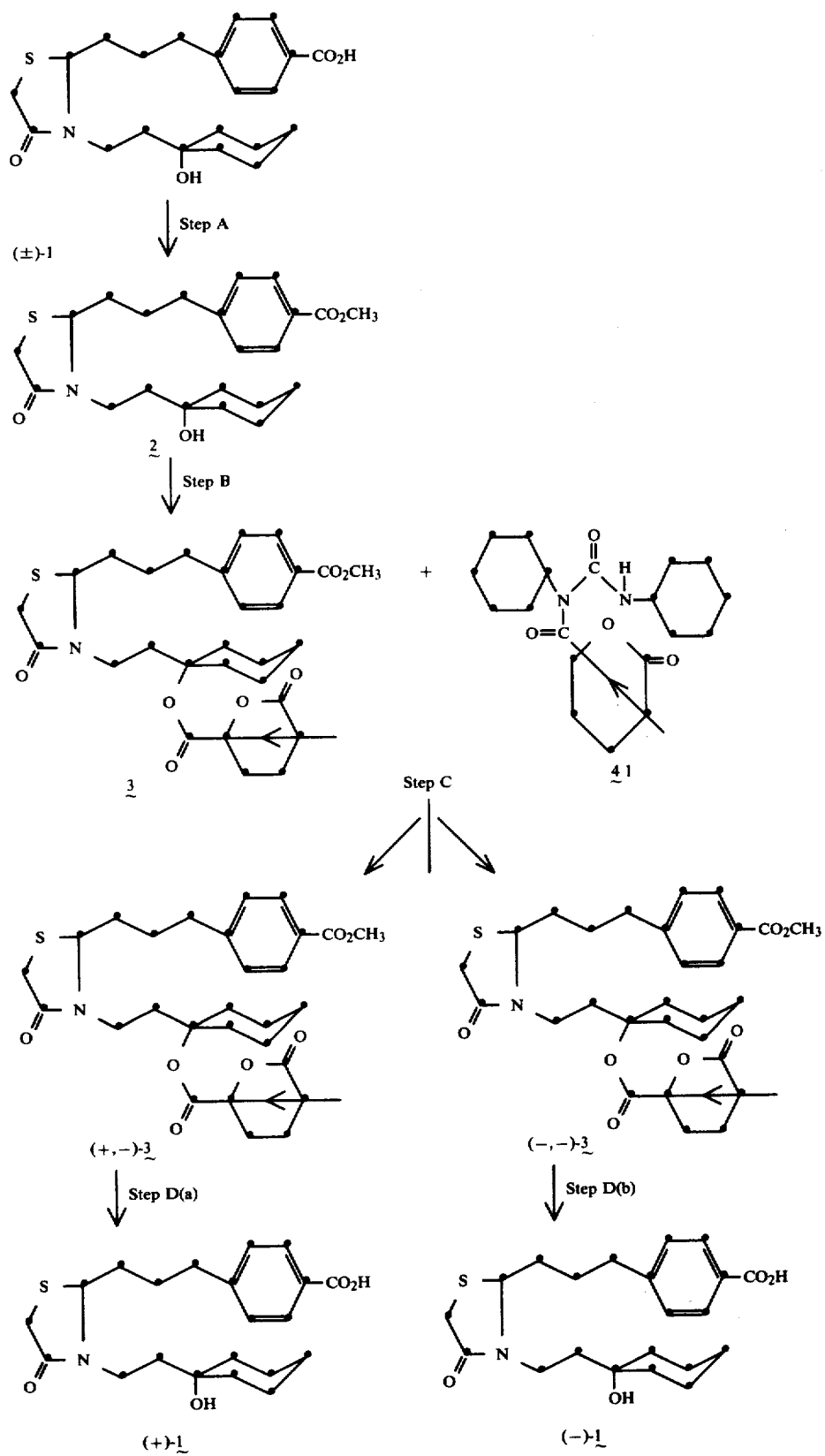
[1] This byproduct acylurea 4 is separable by chromatography.

As outlined above in the flow scheme, the present process consists of four steps:

STEP A

Protection of the benzoic acid

The benzoic acid is generally protected as an ester which can be removed easily via hydrolysis under mild conditions. Thus interphenylene-9-thia-11-oxo-12-aza-prostanoic acid is treated with an esterifying agent such as, for example, an alcohol or an alkyl halide in the presence of a catalyst to form a benzoate of the structural formula

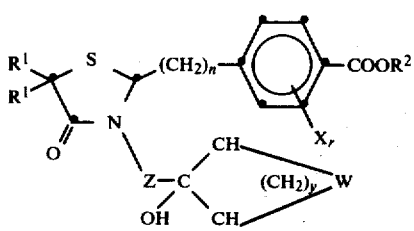

wherein $R^2$ is as described in, the following (1) Description which summarizes the scope of esterification with an alcohol; and (2) Description which summarizes the scope of esterification with a halide.

(1) Esterification of the Benzoic Acid with an Alcohol Alcohol ($R^2OH$)

(a) $C_{1-5}$ alkanol wherein $R^2$ is methyl, ethyl, isopropyl, tertiary butyl; isoamyl or the like; or (b) phenyl-substituted methanol, e.g., benzyl alcohol, benzhydryl, or diphenylmethyl alcohol.

Catalyst under acidic conditions (a) sulfuric acid alone or in the presence of molecular sieves or arylsulfonic acids such as phenylsulfonic acid;

(b) hydrochloric acid or hydrobromic acid; or (c) boron trifluoride-etherate.

Catalyst under neutral or basic conditions

N,N'-dicyclohexylcarbodiimide;
β-trichloromethyl-β-propiolactone;
N,N'-carbonyldiimidazole;
triphenylphosphine and diethylazodicarboxylate;
1-methyl-2-chloropyridinium iodide; or
6-chloro-1-p-chlorobenzenesulfonyloxybenzotriazole.

The preferred alcohol to be used is methanol or benzyl alcohol. The reaction is usually carried out in an excess amount of an alcohol in the presence of a catalyst. Under acidic conditions, the preferred catalysts are boron trifluoride etherate and sulfuric acid-molecular sieve. A typical procedure involves the refluxing of the benzoic aid, for example, compound 1, in an alcohol with a suitable catalyst under anhydrous conditions. The refluxing continues with or without stirring until a substantial amount of the acid is converted to the ester. Usually it requires about 0.5 to 48 hours, preferably about 2 to 6 hours to obtain optimal yield. Generally, reaction temperatures vary with the boiling point of the alcohol being used but can be adjusted to a range from about 25° C. to about 120° C. with the optional addition of an inert solvent, for example, diethyl ether, methylene chloride, benzene, toluene or xylene. The preferred temperatures are about 35° C. to about 80° C., since the thiazolidine ring of the compounds of this invention normally survives at such mild temperatures.

(2) Esterification with an Alkyl Halide ($R^3X$)

As to esterification with alkylhalides, the benzoic acid is treated with a base to form a salt before subsequent treatment with an alkylhalide.

(a) $C_{1-5}$ alkylhalides wherein $R^5$ is methyl, ethyl, n-propyl, n-butyl or isoamyl; and X is chloro, bromo or iodo; or (b) benzyl chloride or the like.

Base for converting the benzoic acid to a salt (a) a mineral base such as sodium hydroxide, potassium hydroxide, calcium hydroxide, sodium carbonate or potassium carbonate; or (b) an organic base such as ammonium hydroxide, quaternary ammonium hydroxide, for example, tetramethylammonium hydroxide, tetraethylammonium hydroxide or phenyltrimethylammonium hydroxide.

The reaction is preferably carried out in a polar, aprotic solvent such as dimethylformamide (DMF), N,N-dimethylacetamide (DMAC), dimethylsulfoxide (DMSO), or hexamethylphosphoramide (HMPA). Other polar solvents may also be used. To minimize elimination, primary alkyl halides preferably methyl iodide or benzyl chloride are usually used and prolonged heating at high temperatures should be avoided. In most cases the reaction is conducted at about 0°–100° C. preferably at about 10°–40° C. For example, the reaction is stirred and maintained at about 25° C. until it is substantially complete, usually in about 1 to 48 hrs, preferably about 2 to about 10 hours under optimal conditions.

STEP B

Formation of diastereoisomers

Esterification of the sterically hindered cyclohexyl hydroxyl group is accomplished by treating the product from Step A with an optically active acid generally in the presence of a base and a catalyst. Useful optically active acids, catalysts and bases are described below:

1. Optically active acids (+) or (−)-camphanic acid
(+) or (−)-camphanyl anhydride
(+) or (−)-camphorcarboxylic acid 2. Reagents for Esterification Involving Camphanic Acid or Camphorcarboxylic Acid In the Presence of An Organic Base

Catalyst

N,N'-dicyclohexylcarbodiimide (DCC)
β-tri-chloromethyl-β-propiolactone
N,N'-carbonyldiimidazole
1-methyl-2-halopyridinium iodide
(halo=F, Cl, Br or I)

Base a trialkylamine ($R_3N$) wherein R is alkyl especially $C_{1-5}$alkyl such as methyl, ethyl or butyl
pyridine
4-dimethylaminopyridine
2,4,6-collidine
2,6-lutidine
quinoline

STEP C

Separation of the diastereoisomers

Fractional recrystallization is used to separate the diastereoisomers from Step (B) having the structural formula

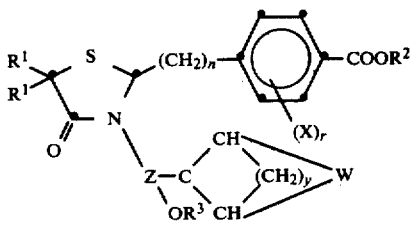

Typically, a suitable organic solvent is selected for successive recrystallization until an optically pure diastereoisomer is isolated. The solvents usually include water, acetonitrile, $C_{1-3}$ alkanol such as methanol or ethanol, acetone, methylacetate, ethylacetate, methylene chloride, ethyl ether, chloroform, dioxane, carbon tetrachloride, toluene, benzene, petroleum ether, n-pentane, n-hexane, cyclohexane or a mixture thereof. The preferred solvent for the camphanyl or camphorcarbonyl esters of the present invention is methylene chloride, chloroform, ethylacetate or a mixture thereof.

STEP D

Hydrolysis

Hydrolysis of the highly hindered esters; for example, camphanyl esters, $(-,-)$-3 is difficult. A few representative hydrolysis procedures which are useful are described below:

TABLE VI

| | Hydrolysis | |
|---|---|---|
| | Catalyst | Solvent |
| (1) | Sodium hydroxide (aqueous solution) | tetrahydrofuran-methanol-water |
| (2) | potassium hydroxide (aqueous solution) | tetrahydrofuran-methanol-water |
| (3) | potassium hydroxide (pellets) and dicyclohexyl-189-crown-6 (naked hydroxide ion) or sodium hydroxide pellets with other crown ethers | toluene or benzene |
| (4) | lithium tetrahydroboron | tetrahydrofuran, or hexamethyl phosphoramide (HMPA) or mixture thereof |

The hydrolysis is usually conducted at about 25° C. to about 120° C. depending on the solvent being used. For example, hydrolysis involving the naked hydroxyl ion (KOH-crown ether) is carried out preferably at about 40° C. to about 60° C. The reaction is continued with vigorous agitation until it is substantially complete, usually about 2 to 48 hours, preferably about 5 to about 24 hours.

The following example illustrates but does not limit the process of the present invention. The underlined numbers in the example identify the products as shown in the Flow Sheet above.

EXAMPLE 1

Resolution of Racemic 4{3-[3-[2-(1-hydroxycyclohexyl)ethyl]-4-oxo-2-thiazolidinyl]propyl}benzoic Acid

Step A. Preparation of (±)-Methyl 4-{3-[3-[2-(1-Hydroxycyclohexyl)ethyl]-4-oxo-2-thiazolidinyl]propyl}benzoate (2)

To a freshly-prepared solution of (±)-4-{3-[3-[2-(1-hydroxycyclohexyl)ethyl]-4-oxo-2-thiazolidinyl]-propyl}benzoic acid (1) (10 g, 25.6 mmol) in dry N,N-dimethylformamide (86 ml) contained in a 250 ml round bottom flask is added finely-ground potassium carbonate (3.54 g, 25.6 mmol) followed by methyl iodide (1.6 ml, 25.6 mmol). The resulting suspension is protected from atmospheric moisture with a magnesium sulfate drying tube and is stirred at room temperature for 19.5 hours. The reaction mixture is poured into water (175 ml) contained in a separatory funnel and then is extracted with ether (3×40 ml). The organic extracts are combined, washed with saturated aqueous sodium bicarbonate (3×30 ml), dried over sodium sulfate and filtered. Evaporation (in vacuo) of the filtrate leaves the desired ester 2 as a pale yellow oil (10.55 g); tlc, $R_f$=0.4 (homogeneous, UV detection) on silica gel with ethyl acetate:hexane (7:3; v:v) as eluent; ir (2% solution in chloroform) 3400 (w), 1710 (s), 1600 (s) and 1280 (s) cm$^{-1}$.

Step B. Preparation of Methyl 4-{3-[3-[2-(1-(−)-camphanyloxy)cyclohexyl)-ethyl]-4-oxo-2-thiazolidinyl]propyl}benzoate (3)

To a solution of (±)-methyl 4-{3-[3-[2-(1-hydroxycyclohexyl)ethyl]-4-oxo-2-thiazolidinyl]propyl}-benzoate (2) (38.37 g, 94.6 mmol) in methylene chloride (189 ml) are added (−)-camphanic acid (20.64 g, 104.1 mmol) and 4-dimethylaminopyridine (5.77 g, 47.3 mmol). The resulting solution is cooled to 0° C. and treated with a solution of N,N'-dicyclohexylcarbodiimide (23.38 g, 113.52 mmol) in methylene chloride (180 ml) added slowly with stirring over 15 min. Thereby is obtained a heterogeneous mixture which is stirred at ambient temperature for 22 h. The reaction mixture is filtered to remove the insoluble solid (N,N'-dicyclohexylurea). The filtrate is washed with 0.2 N hydrochloric acid (2×60 ml) and water (2×80 ml), dried over sodium sulfate and filtered. Evaporation (in vacuo) of the filtrate affords a brown, oily residue (semi-solid): tlc on silica gel with chloroform:methanol (98:2; v:v) indicates that the product 3, $R_f$=0.3, is accompanied by starting material 2 (ca. 5%) and traces of 4-dimethylaminopyridine.

The oily residue is "flash chromatographed" on silica gel (600 g, 230–400 mesh, E. Merck) using chloroform-methanol (98:2; v:v) as eluent and a flow rate sufficient to move the solvent front at 1″ per min. Thereby is eluted product 3 (ca. 55 g as a yellow solid) which is contaminated with N-((−)-camphanyl)-N,N'-dicyclohexylurea (4). Product 3 is used as such in Step C described below.

Step C. Separation of Mixture 3 Into Diastereomeric Components (−,−)-3 and (+,−)-3

(a) Isolation of (−,−)-3-Yellow solid 3 (ca. 55 g from Step B above) is triturated with ethyl acetate:hexane (1:1; v:v; 300 ml) at room temperature for 1 h to provide a heterogeneous mixture which is filtered. The collected, pale yellow solid (ca. 25 g of impure (−,−)-3) is recrystallized six times from ethyl acetate to afford pure diastereomer[1] (−,−)-3 as colorless crystals (8.85 g), mp 163°–164° C.; $[\alpha]_D^{22} = -47.3°$ (c 0.58, CHCl$_3$).

[1] Pmr analysis of (−,−)-3 and (+,−)-3 using the Europium shift reagent Eu(fOd)$_3$ shows that each of these materials is a single diastereomer.

(b) Isolation of (+,−)-3-The trituration filtrate from Step C (a) above is evaporated in vacuo to provide a residue[2] (ca. 24 g) consisting essentially of (+,−)-3 and byproduct 4. This residue is "flash chromatographed" in two separate 12 g portions as described below. A 12 g portion is applied in chloroform to a silica gel column (ca. 350 g, 230–400 mesh, E. Merck, 60 mm in diameter × 10" in length) which is eluted first with 30% ethyl acetate in hexane (2.4 L) at a flow rate sufficient to move the solvent front 1" per min to remove the byproduct 4. Continued elution at the same flow rate with 40% ethyl acetate in hexane (1 L), 50% ethyl acetate in hexane (2 L) and 60% ethyl acetate in hexane (1 L) provides (+,−)-3. From the two "flash chromatographies" is obtained a pale yellow solid (15 g), $[\alpha]_D^{22} = +26.5°$ (c 0.57, CHCl$_3$). This solid is recrystallized from ethyl acetate to constant rotation. Thereby is obtained pure diastereomer (+,−)-3[3] as colorless crystals (10.55 g), mp 130°–132° C.; $[\alpha]_D^{22} = +37.2°$ (c 0.61, CHCl$_3$).

[2] This residue can be analyzed by tlc: R$_f$=0.12 for (+,−)-3 and R$_f$=0.36 for 4 on silica gel with ethyl acetate:hexane (3:7; v:v) elution followed by detection (dipping tlc plate in 5% sulfuric acid in ethanol and subsequent heating on a hot plate).
[3] See footnote 1 from previous paragraph.

Step D. Hydrolysis of (+,−)-3 and (−,−)-3

(a) Preparation of
(+)-4-{3-[3-[2-(1-Hydroxycyclohexyl)ethyl]-4-oxo-2-thiazolidinyl]propyl}benzoic Acid To toluene (102 ml) contained in a 250 ml round bottom flask is added crushed solid potassium hydroxide (3.83 g, 68.3 mmol). The resulting heterogeneous mixture is heated at reflux until ca. 20 ml of distillate is collected[4] and then is cooled to room temperature. To the cooled heterogeneous mixture is added (+,−)-3 (4 g, 6.83 mmol) followed by dicyclohexyl-18-Crown-6 (12.72 g, 34.2 mmol). The resulting reaction mixture is protected from atmospheric moisture with a magnesium sulfate drying tube and is vigorously stirred and heated at 40° C. (oil bath) for 1 h. Then the drying tube is removed, water (80 ml) is added to the brown reaction mixture and stirring and heating at 40° C. are continued for 45 h. After cooling to room temperature, the reaction mixture is poured slowly into cold, excess N hydrochloric acid (200 ml) with vigorous stirring. The acidic,[5] aqueous mixture is transferred to a separatory funnel and the layers are allowed to separate. The aqueous layer (acidic phase) is extracted with chloroform (4×100 ml). The toluene and chloroform layers are combined, washed with water (2×100 ml), dried over sodium sulfate and filtered. Evaporation (in vacuo) of the filtrate leaves an oily residue which is triturated with ether at room temperature to afford an insoluble, colorless solid. The solid is collected, washed with ether and dried to give 2.04 g (76%) of (+)-1: tlc, R$_f$=0.26 (homogeneous, UV detection) with chloroform:methanol (9:1; v:v) on silica gel; identical by tlc to 1. Recrystallization from methanol affords pure enantiomer (+)-1 as colorless crystals (1.1 g), mp 139.5°–140.5° C.; $[\alpha]_D^{22} + 70.0°$ (c 0.47, CHCl$_3$); ir (KBr pellet) 3270, 1690, 1640 and 1260 cm$^1$; pmr (CDCl$_3$)δ 8.05 (2H, d), 7.28 (2H, d), 6.49 (2H, bs, OH and CO$_2$H), 4.75 (H, bm), 3.56 (2H, s), 2.68 (2H, t) and 1.60 (bc envelope).

[4] Azeotropic distillation ensures the removal of traces of moisture.
[5] The pH of this aqueous mixture should be checked with Congo red test paper; if not sufficiently acidic, additional 0.1 N hydrochloric acid should be added prior to separation of the layers.

Anal. Calcd. for C$_{21}$H$_{29}$NO$_4$S: C, 64.42; H, 7.47; N, 3.58. Found: C, 64.57; H, 7.81; N, 3.51.

(b) Preparation of
(−)-4-{3-[3-[2-(1-hydroxycyclohexyl)ethyl]-4-oxo-2-thiazolidinyl]propyl}benzoic Acid The hydrolysis of the pure diastereomer (−,−)-3 is carried out exactly as described above for (+,−)-3 in Step D (a). Thereby is obtained pure enantiomer (−)-1 as colorless crystals (1.24 g), mp 140°–141° C. (from CH$_3$OH); $[\alpha]_D^{22} - 68.7°$ (C 0.47, CHCl$_3$); tlc, ir and pmr data identical with those recorded for (+)-1.

Anal. Calcd. for C$_{21}$H$_{29}$NO$_4$S: C, 64.42; H, 7.47; N, 3.58. Found: C, 64.48; H, 7.72; N, 3.72.

Using substantially the same procedure as in Example 1 but substituting an equivalent amount of camphorcarboxylic acid for the camphanic acid, the corresponding camphor carbonyl esters are obtained and after separation and hydrolysis, comparable yields of the enantiomers of the azaprostanoic acid are obtained.

Following substantially the same procedure as described in Example 1, but substituting for the racemic combinations used therein the following unresolved compounds:

4-{3-[3-[2-(1-hydroxycyclohexyl)ethyl]-4-oxo-2-thiazolidinyl]propyl}benzoic acid;

4-{3-[3-[2-(1-hydroxycyclopentyl)ethyl]-4-oxo-2-thiazolidinyl]propyl}benzoic acid;

4-{3-[3-[2-(1-hydroxycycloheptyl)ethyl]-4-oxo-2-thiazolidinyl]propyl}benzoic acid;

4-{3-[3-[2-(1-hydroxy-4,4-dimethylcyclohexyl)ethyl]-4-oxo-2-thiazolidinyl]propyl}benzoic acid;

4-{3-[3-[2-(9-hydroxy-9-bicyclo[3.3.1]nonyl)ethyl]-4-oxo-2-thiazolidinyl]propyl}benzoic acid;

4-{4-[3-[2-(1-hydroxycyclohexyl)ethyl]-4-oxo-2-thiazolidinyl]butyl}benzoic acid;

4-{3-[3-[3-(1-hydroxycyclohexyl)propyl]-4-oxo-2-thiazolidinyl]propyl}benzoic acid;

4-{3-[3-[3-(1-hydroxycyclohexyl)-trans-2-propenyl]-4-oxo-2-thiazolidinyl]propyl}benzoic acid;

4-{3-[3-[3-(1-hydroxycyclohexyl)-cis-2-propenyl]-4-oxo-2-thiazolidinyl]propyl}benzoic acid;

4-{3-[3-[3-(1-hydroxycyclohexyl)-2-propynyl]-4-oxo-2-thiazolidinyl]propyl}benzoic acid;

4-{3-[3-[2-(1-hydroxycyclohexyl)-ethyl]-4-oxo-2-thiazolidinyl]propyl}-3-chlorobenzoic acid;

4-{3-[3-[2-(1-hydroxycyclohexyl)-ethyl]-4-oxo-2-thiazolidinyl]propyl}-2-chlorobenzoic acid;

4-{3-[3-[2-(1-hydroxycyclohexyl)-ethyl]-4-oxo-2-thiazolidinyl]propyl}-3-methylbenzoic acid;

4-{3-[3-[2-(1-hydroxycyclohexyl)-ethyl]-5,5-dimethyl-4-oxo-2-thiazolidinyl]propyl}benzoic acid; or 4-{3-[3-[2-(1-hydroxycyclohexyl)-ethyl]-5,5-dideuterio-4-oxo-2-thiazolidinyl]propyl}benzoic acid;

there are obtained the corresponding enantiomers:

(+) or (−)-4-{3-[3-[2-(1-hydroxycyclohexyl)ethyl]-4-oxo-2-thiazolidinyl]propyl}benzoic acid;

(+) or (−)-4-{3-[3-[2-(1-hydroxycyclopentyl)ethyl]-4-oxo-2-thiazolidinyl]propyl}benzoic acid;

(+) or (−)-4-{3-[3-[2-(1-hydroxycycloheptyl)etuyl]-4-oxo-2-thiazolidinyl]propyl}benzoic acid;

(+) or (−)-4-{3-[3-[2-(1-hydroxy-4,4-dimethylcyclohexyl)ethyl]-4-oxo-2-thiazolidinyl]propyl}benzoic acid;

(+) or (−)-4-{3-[3-[2-(9-hydroxy-9-bicyclo[3.3.1-]nonyl)ethyl]-4-oxo-2-thiazolidinyl]propyl}benzoic acid;

(+) or (−)-4-{4-[3-[2-(1-hydroxycyclohexyl)ethyl]-4-oxo-2-thiazolidinyl]butyl}benzoic acid;

(+) or (−)-4-{3-[3-[3-(1-hydroxycyclohexyl)propyl]-4-oxo-2-thiazolidinyl]propyl}benzoic acid;

(+) or (−)-4-{3-[3-[3-(1-hydroxycyclohexyl)-trans-2-propenyl]-4-oxo-2-thiazolidinyl]propyl}benzoic acid;

(+) or (−)-4-{3-[3-[3-(1-hydroxycyclohexyl)-cis-2-propenyl]-4-oxo-2-thiazolidinyl]propyl}benzoic acid;

(+) or (−)-4-{3-[3-[3-(1-hydroxycyclohexyl)-2-propynyl]-4-oxo-2-thiazolidinyl]propyl}benzoic acid;

(+) or (−)-4-{3-[3-[2-(1-hydroxycyclohexyl)ethyl]-4-oxo-2-thiazolidinyl]propyl}-3-chlorobenzoic acid;

(+) or (−)-4-{3-[3-[2-(1-hydroxycyclohexyl)ethyl]-4-oxo-2-thiazolidinyl]propyl}-2-chlorobenzoic acid;

(+) or (−)-4-{3-[3-[2-(1-hydroxycyclohexyl)ethyl]-4-oxo-2-thiazolidinyl]propyl}-3-methylbenzoic acid;

(+) or (−)-4-{3-[3-[2-(1-hydroxycyclohexyl)ethyl]-5,5-dimethyl-4-oxo-2-thiazolidinyl]propyl}benzoic acid; and (+) or (−)-4-{3-[3-[2-(1-hydroxycyclohexyl)ethyl]-5,5-dideuterio-4-oxo-2-thiazolidinyl]propyl}benzoic acid.

In addition to the present resolution process, other embodiments of the present invention are (1) the diastereomers illustrated by (+,−)-3 and (−,−)-3 in the Flow Sheet and (2) the individual enantiomers of the Formula I compound which have pharmaceutical activity, e.g. as renal vasodilators.

Claims to the invention follow.

What is claimed is:

1. A diastereomeric ester having the formula

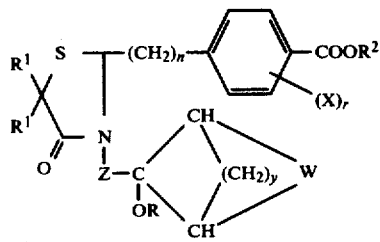

wherein
(1) X is chlorine or methyl;
(2) r is 0, 1 or 2;
(3) n is 3 or 4;
(4) $R^1$ is hydrogen, deuterium or methyl;
(5) $R^2$ is alkyl, benzyl or diphenylmethyl;
(6) $R^3$ is camphanyl or camphor carbonyl;
(7) Z is ethylene, trimethylene, cis or transpropenylene or propynylene;
(8) y is 0, 1 or 2 and
(9) W is polymethylene of 2–6 carbon atoms.

2. The diastereomeric ester of claim 1 having the structural formula:

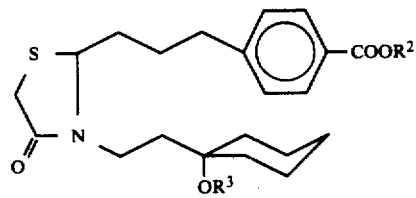

3. Diastereomeric methyl 4-{3-[3-[2-(1-((−)-camphanyloxy)cyclohexyl)ethyl]-4-oxo-2-thiazolidinyl]propyl}benzoate, an ester of claim 1.